United States Patent [19]

Bohn et al.

[11] Patent Number: 5,264,206

[45] Date of Patent: * Nov. 23, 1993

[54] NAIL LACQUER WITH ANTIMYCOTIC ACTIVITY, AND A PROCESS FOR THE PREPARATION THEREOF

[75] Inventors: Manfred Bohn; Walter Dittmar, both of Hofheim am Taunus; Karl Kraemer, Langen; Heinz G. Peil, Bad Nauheim; Eberhard Futterer, Kelkheim, all of Fed. Rep. of Germany

[73] Assignee: Hoechst Aktiengesellschaft, Frankfurt am Main, Fed. Rep. of Germany

[*] Notice: The portion of the term of this patent subsequent to Sep. 18, 2007 has been disclaimed.

[21] Appl. No.: 206,363

[22] Filed: Jun. 14, 1988

[30] Foreign Application Priority Data

Jun. 16, 1987 [DE] Fed. Rep. of Germany ....... 3720147

[51] Int. Cl.$^5$ ................... A61K 7/043; A61K 31/135; A61K 31/325; A61K 31/415
[52] U.S. Cl. ...................... 424/61; 514/396; 514/397; 514/444; 514/481; 514/657
[58] Field of Search ............................. 424/61, 78, 81

[56] References Cited

U.S. PATENT DOCUMENTS

| 3,912,666 | 10/1975 | Spitzer et al. | 521/132 |
| 4,472,421 | 2/1984 | Buchel et al. | 424/273 R |
| 4,957,730 | 9/1990 | Bohn et al. | 424/61 |

FOREIGN PATENT DOCUMENTS

| 1175355 | 4/1984 | Canada . | |
| 055397 | 11/1981 | European Pat. Off. . | |
| 0064830 | 11/1982 | European Pat. Off. | 424/61 |
| 0085370 | 10/1983 | European Pat. Off. | 424/61 |
| 2430039 | 3/1976 | Fed. Rep. of Germany . | |
| 2073229 | 10/1981 | United Kingdom | 424/61 |
| 8702580 | 7/1987 | World Int. Prop. O. . | |

OTHER PUBLICATIONS

Board of Appeals decision in Ser. No. 942,699, now U.S. Pat. No. 4,957,730.

Primary Examiner—Robert A. Wax
Assistant Examiner—Eric Grimes
Attorney, Agent, or Firm—Finnegan, Henderson, Farabow, Garrett & Dunner

[57] ABSTRACT

A nail lacquer containing at least one film-former which is insoluble in water and at least one substance which has antimycotic activity and is from the group comprising tioconazole, econazole, oxiconazole, miconazole, tolnaftate and naftifine hydrochloride.

12 Claims, No Drawings

NAIL LACQUER WITH ANTIMYCOTIC ACTIVITY, AND A PROCESS FOR THE PREPARATION THEREOF

Mycoses of the nails (onychomycoses) are intractable types of disease which it has hitherto not been possible to treat satisfactorily. The term onychomycoses embraces various types of mycoses of the nails, of which those caused by dermatophytes are the most difficult to treat, whereas the mycoses of the nails caused by yeast-like fungi have hitherto been those which it has been possible most readily to treat successfully.

The difficulty with onychomycoses caused by dermatophytes is additionally that they make a considerable contribution to the spread of infectious fungi. Various routes have been followed hitherto for their treatment, but without permanent success.

One method of treatment, namely systemic treatment, consisted in oral administrations of antifungal agents. This required long-term treatment, which experience shows to be a potential cause of intoxication effects.

Another method comprises removal of the nails surgically or by the action of chemicals, in the hope that healthy uninfected nails will subsequently grow. This method is by its nature very aggressive and, moreover, does not guarantee that the nails will subsequently grow in the natural shape; on the contrary, the nails which subsequently grow are often deformed.

A third, but conservative, method comprises topical treatment of the nails with specific substances having antimycotic activity. A very wide variety of treatment methods has been tried for this. Thus, in a combined treatment, the nails have initially been treated with solutions of the substances having antimycotic activity, and cream dressings have been applied each night. This treatment method is by its nature also very unpleasant for, and a psychological strain on, the patient. On the one hand, the nails have to be treated with solutions several times a day. On the other, they have to be provided with dressings, particularly at night. Furthermore, it is necessary for the diseased nails to be filed down continually, which not only is troublesome but also contributes to spreading the pathogens. The results of all this are that many of the patients do not persist with the treatment, which usually takes several months; on the contrary, they become discouraged and negligent, and thus the therapy is unsuccessful. Also detrimental to the success of treatment by this method is that the solutions and creams are usually miscible with water or hydrophilic and thus can be removed again from the surface of the nail or dissolved out of the nail on washing, bathing and showering, and thus may need to be reapplied thereafter.

Thus, great hopes have been placed in a quite different method, namely in treatment with a nail lacquer which contains the substance sulbentine which has antimycotic activity, and nitrocellulose as film-former; sulbentine is a thiadiazine compound of the formula

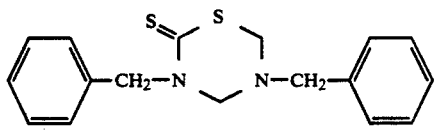

Although this method has been practiced now for about 20 years, it has not been used generally for therapy because in practice only relatively mild mycoses of the nails can be controlled with these nail lacquers. The success of this formulation has presumably been unsatisfactory inter alia because of the lack of adequate bioavailability of the active substance from the solid system present after the lacquer has dried.

For this reason, many cases, especially the more severe ones, have continued to be treated with the surgical or chemical methods described above or with the combined solution and cream therapy.

A crucial advance in the treatment and prevention of mycoses of the nails was achieved by applying to the nails, in particular to the diseased nails, the nail lacquer proposed in Patent Application P 35 44 983.7 (HOE 85/F 287), which corresponds to copending U.S. patent application Ser. No. 942,699 filed Dec. 17, 1986, now U.S. Pat. No. 4,957,730; this nail lacquer is distinguished by containing a film-former which is insoluble in water and at least one 1-hydroxy-2-pyridone (as substance having antimycotic activity) of the following formula:

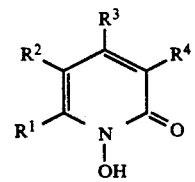

In the formula, $R^1$ denotes a "saturated" hydrocarbon radical having 6 to 9, preferably 6 to 8, carbon atoms, one of the radicals $R^2$ and $R^4$ denotes a hydrogen atom, and the other denotes H, $CH_3$ or $C_2H_5$, and $R^3$ denotes an alkyl radical having 1 or 2 carbon atoms.

The term "saturated" in this connection designates those radicals which contain no ethylenic or acetylenic bonds.

The active substances can be present both in free form and in the form of their salts.

Using this nail lacquer it is possible to achieve an effective cure in the treatment of mycoses of the nails, with the nail usually growing again subsequently without deformation. In view of the previous poor results of therapy, this is an extremely important finding.

The nail lacquer is also suitable for prophylactic use against mycoses of the nails, with a sufficiently high active substance depot being obtained in the nail for there to be, if fungal contamination takes place, no outbreak of nail disease caused by fungi.

During further investigations in this specialist area it has now been found that similar advantages can also be achieved by use of a nail lacquer containing at least one special film-former which is insoluble in water and at least one special imidazole, thiocarbamic acid or propenylnaphthalenemethaneamine derivative as substance having antimycotic activity.

Hence the invention relates to a nail lacquer containing at least one film-former which is insoluble in water and at least one substance having antimycotic activity; the features of the nail lacquer are that the film-former which is insoluble in water is selected from the group comprising polyvinyl acetate, partially hydrolyzed polyvinyl acetate, copolymers of vinyl acetate on the one hand and acrylic acid or crotonic acid or monoalkyl maleates on the other hand, ternary copolymers of vinyl acetate on the one hand and crotonic acid and vinyl neodecanoate on the other hand, ternary copolymers of vinyl acetate on the one hand and crotonic acid and vinyl propionate on the other hand, copolymers of methyl vinyl ether and monoalkyl maleates, copolymers of fatty acid vinyl esters and acrylic acid or methacrylic acid, copolymers of N-vinylpyrrolidone, methacrylic acid and alkyl methacrylates, copolymers of acrylic acid and methacrylic acid or alkyl acrylates or alkyl methacrylates, polyvinyl acetals, polyvinyl butyrals, alkyl-substituted poly-N-vinylpyrrolidones, and alkyl esters of copolymers of olefins and maleic anhydride, and that the substances having antimycotic activity are selected from the following group:

Tioconazole (an imidazole derivative):

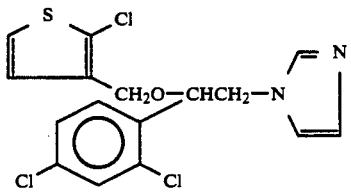

Econazole (an imidazole derivative):

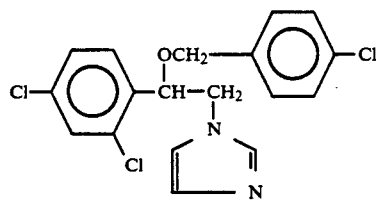

Oxiconazole (an imidazole derivative):

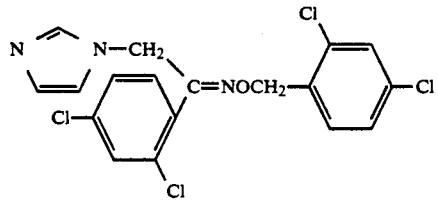

Miconazole (an imidazole derivative):

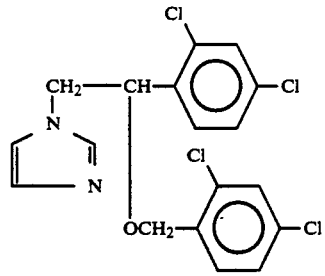

Tolnaftate (a thiocarbamic acid derivative):

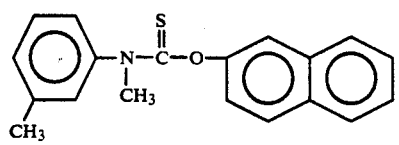

Naftifine hydrochloride (a propenylnaphthalene-methaneamine derivative):

-continued

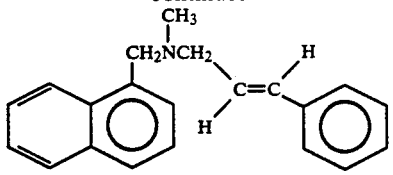

The film-formers which are insoluble in water are substantially identical to the film-formers specified in the abovementioned patent application. The alkyl radicals in the esters are usually short-chain and mostly have no more than 4 carbon atoms. Where the film-formers contain units of methacrylic acid or methacrylic acid derivatives, it is advantageous for these not to amount to more than about 15 mot% of the total polymer.

It is possible, where appropriate, for the abovementioned film-formers which are insoluble in water also to be, or to have been, mixed with cellulose nitrate; however, in this case the cellulose nitrate should not account for more than a maximum of about 50% by weight of the total film-former component.

A preferred film-former which is insoluble in water is the copolymer of methyl vinyl ether and monoalkyl maleate—preferably mono-n-butyl maleate. The units of the two components are preferably contained in this copolymer in approximately the same proportion.

The antimycotic substances present in the nail lacquer according to the invention are known compounds whose antimycotic properties are likewise known. Antimycotic substances preferred in this connection are tioconazole and/or econazole. The substances can be used both singly and mixed with one another; the salts can likewise be used.

The content of active substance in the nail lacquer according to the invention depends on the structure of each active substance and thus on its release from the lacquer film, on its penetration behavior in the nail and on its antimicrobial properties.

The nail lacquer according to the invention is preferably used as a medicinal nail lacquer which contains an amount of the antimycotic active substance which is effective and suffices to kill the dermatophytes causing the mycosis of the nails.

The content of active substance in the nail lacquer—that is to say in the use form containing solvent—is generally about 0.5 to 20, preferably of about 2 to 15, % by weight.

In the nail lacquers according to the invention, the content of active substance is generally about 2 to 80, preferably of about 10 to 60, and in particular of about 20 to 40, % by weight, in each case based on the amount of non-volatile ingredients—i.e. the total of film-formers, and of pigments, plasticizers and other non-volatile additives which are present where appropriate, together with active substance.

Suitable solvents for the nail lacquer according to the invention are substances such as hydrocarbons, halogenated hydrocarbons, alcohols, ethers, ketones and esters customary in cosmetics, especially acetic and esters of monohydric alcohols (ethyl acetate, n-butyl acetate etc.), where appropriate mixed with aromatic hydrocarbons such as toluene and/or alcohols such as ethanol or isopropanol and/or aliphatic sulfoxides and sulfones such as, for example, dimethyl sulfoxide or sulfolane.

The combination of the solvents is known to be of crucial importance for the drying time, ease of spreading and other important properties of the lacquer or lacquer film. The solvent system is preferably composed of an optimal mixture of low-boilers (=solvents with a boiling point up to about 100° C.) and medium-boilers (=solvents with a boiling point up to about 150° C.), where appropriate with a small proportion of high-boilers (=solvents with a boiling point above about 150° C.).

The nail lacquers according to the invention can also contain additives common in cosmetics, such as plasticizers based on phthalates or camphor, colorants or pigments, perlescent agents, sedimentation retardants, sulfonamide resins, silicates, perfumes, wetting agents such as sodium dioctylsulfosuccinate, lanolin derivatives, sunscreen agents such as 2-hydroxy-4-methoxybenzophenone, substances having antibacterial activity, and substances with a keratolytic and/or keratoplastic action, such as ammonium sulfite, esters and salts of thioglycolic acid, urea, allantoin, enzymes and salicylic acid.

Colored or pigmented nail lacquers have, for example, the advantage that the formulation according to the invention can be matched to the esthetic sense of the patient.

The nail lacquer is prepared in a customary manner by mixing the individual components and carrying out—where necessary—further processing appropriate for the particular formulation.

The nail lacquers according to the invention also differ fundamentally from the antimycotic agents which are disclosed in European Patent 55,397 and which contain, as active substances, azole derivatives, in particular imidazole and triazole derivatives. These antimycotic agents are intended to be applied as a water-soluble film, to have a depot action and to permit short-duration therapy. They are said also to be suitable for the treatment of mycoses of the nails and to be used both in solutions and in sprays which, after drying, form a water-soluble film. The use of such water-soluble binders results, by its nature, in more or less of the agent which has been applied being removed at each wash.

The use of film-forming polymers which are insoluble in water according to the present invention contrasts drastically with the statement in EP-B 55,397, according to which the mycosis is aggravated if polymers insoluble in water, for example "methacrylates" are used in place of the formulations which are described therein and use water-soluble polymers. Admittedly the known sulbentine-containing nail lacquer contains a film-former which is insoluble in water, namely nitrocellulose; however, as mentioned in the introduction, the nail lacquer has not found wide use because of its deficient antimycotic efficacy. In contrast, the mycosis of the nail can be treated successfully with the aid of the nail lacquers according to the invention, which contain film-forming polymers which become insoluble in water after drying.

The efficacy of the nail lacquers according to the invention was tested on keratinized excized pig skin. The test method which is employed permits the release of the active substances from the solid system which is present after the nail lacquer has dried, and their ability to penetrate in the keratinized tissue, to be tested.

The present invention is explained in more detail by the examples which follow; the examples also contain a comparison with a sulbentine-containing nail lacquer. The stated percentage amounts are based on weight. P denotes parts by weight.

EXAMPLE 1-6 AND COMPARISON EXAMPLE (WITH SULBENTINE-CONTAINING NAIL LACQUER)

First, fungi of the strain Trichophyton mentagrophytes 109 were inoculated onto the surface of pieces of shaven pig skin and were cultured there. After a preculture lasting 3 days, the fungus had grown into the keratinized tissue. The surface of the skin was then washed and treated at room temperature with 0.5% strength formulations of compounds 1 to 6, in each case dissolved in a mixture of 45 P of isopropanol, 29.5 P of ethyl acetate, 10 P of dimethyl sulfoxide and 15 P of a copolymer of equal molar parts of methyl vinyl ether and mono-n-butyl maleate. After the lacquer formulation had acted for 2 hours, it was removed again from the surface of the skin by pulling off with adhesive tape. The treated keratinized tissue was mechanically homogenized and then, after appropriate dilution, streaked onto agar plates for determination of the organism count.

The same test was also carried out with the comparison substance sulbentine.

The Table which follows lists the results of these experiments. In this, the stated numbers relate to the percentage decrease in the organism units in the treated pieces of skin by comparison with the control growth on untreated skin.

TABLE

| Fungicides (%) on excized skin | | |
| --- | --- | --- |
| Skin: | Pig (back) | |
| Products: | Nail lacquers* containing 0.5% active substance | |
| Example: | 1 Tioconazole | 97.1 |
| | 2 Econazole | 92.9 |
| | 3 Oxiconazole | 88.9 |
| | 4 Miconazole | 85.6 |
| | 5 Tolnaftate | 87.6 |
| | 6 Naftifine hydrochloride | 90.0 |
| Comparison: | Sulbentine | 82.9 |

*Composition of the lacquer base: 45 P of isopropanol, 29.5 P of ethyl acetate, 10 P of dimethyl sulfoxide and 15 P of methyl vinyl ether/mono-butyl maleate copolymer.

EXAMPLES 7-9

The examples which follow give compositions of the nail lacquer formulations according to the invention. The nail lacquers were prepared by dissolving the various components in the solvents.

| | | |
| --- | --- | --- |
| 7. | Isopropyl alcohol | 33.00% |
| | Ethyl acetate | 33.00% |
| | 50% strength solution of a copolymer of methyl vinyl ether and monobutyl maleate in isopropyl alcohol | 30.00% |
| | Tioconazole | 4.00% |
| 8. | Isopropyl alcohol | 55.00% |
| | Ethyl acetate | 32.00% |
| | Water | 4.00% |
| | Cellulose nitrate | 3.10% |
| | Dibutyl phthalate | 0.60% |
| | Polyvinyl butyral | 3.80% |
| | Naftifine hydrochloride | 1.50% |
| 9. | Isopropyl alcohol | 28.70% |
| | Ethyl acetate | 28.60% |
| | Water | 10.70% |
| | 50% strength solution of a copolymer of methyl vinyl ether and monobutyl maleate in isopropyl alcohol | 30.00% |
| | Econazole nitrate | 2.00% |

We claim:

1. A nail lacquer containing at least one film-former which is insoluble in water and at least one substance having antimycotic activity, wherein the film-former which is insoluble in water is selected from the group consisting of polyvinyl acetate, partially hydrolyzed polyvinyl acetate, a copolymer of vinyl acetate and acrylic acid, a copolymer of vinyl acetate and crotonic acid, a copolymer of vinyl acetate and a monoalkyl maleate, a ternary copolymer of vinyl acetate, crotonic acid and vinyl neodecanoate, a ternary copolymer of vinyl acetate, crotonic acid and vinyl propionate, a copolymer of methyl vinyl ether and a monoalkyl maleate, a copolymer of a fatty acid vinyl ester and acrylic acid or methacrylic acid, a copolymer of N-vinylpyrrolidone, methacrylic acid and an alkyl methacrylate, a copolymer of acrylic acid and methacrylic acid or an alkyl acrylate or alkyl methacrylate, a polyvinyl acetal, a polyvinyl butyral, an alkyl-substituted poly-N-vinylpyrrolidone, and an alkyl ester of a copolymer of an olefin and maleic anhydride, and wherein the substance having antimycotic activity is selected from the group consisting of tioconazole, econazole, oxiconazole, miconazole, tolnaftate and naftifine hydrochloride, and is present in an amount effective against nail mycoses.

2. A nail lacquer as claimed in claim 1, wherein the film-former which is insoluble in water is a copolymer of methyl vinyl ether and a monoalkyl maleate.

3. A nail lacquer as claimed in claim 2, wherein the copolymer is mono-n-butyl maleate.

4. A nail lacquer as claimed in claim 1, wherein the substance having antimycotic activity is tioconazole, econazole or a mixture of tioconazole and econazole.

5. A nail lacquer as claimed in claim 1, which is a medicinal nail lacquer which contains an amount of the antimycotic active substance which is effective and suffices to kill dermatophytes which cause mycoses of the nails.

6. A nail lacquer as claimed in claim 1, which contains the active substance in an amount of about 2 to 80% by weight based on the amount of non-volatile ingredients.

7. A nail lacquer as claimed in claim 1, which contains the active substance in an amount of about 10 to 60% by weight based on the amount of non-volatile ingredients.

8. A nail lacquer as claimed in claim 1, which contains the active substance in an amount of about 20 to 40% by weight based on the amount of non-volatile ingredients.

9. A nail lacquer as claimed in claim 1, which contains the active substance in an amount of about 0.5 to 20% by weight based on the amount of volatile and non-volatile ingredients.

10. A nail lacquer as claimed in claim 1, which contains the active substance in an amount of about 2 to 15% by weight based on the amount of volatile and non-volatile ingredients.

11. A process for the preparation of a nail lacquer containing at least one film-former which is insoluble in water and at least one substance having antimycotic activity, which comprises mixing at least one film-former which is insoluble in water and is selected from the group consisting of polyvinyl acetate, partially hydrolyzed polyvinyl acetate, a copolymer of vinyl acetate and acrylic acid, a copolymer of vinyl acetate and crotonic acid, a copolymer of vinyl acetate and a monoalkyl maleate, a ternary copolymer of vinyl acetate, crotonic acid and vinyl neodecanoate, a ternary copolymer of vinyl acetate, crotonic acid and vinyl propionate, a copolymer of methyl vinyl ether and a monoalkyl maleate, a copolymer of a fatty acid vinyl ester and acrylic acid or methacrylic acid, a copolymer of N-vinylpyrrolidone, methacrylic acid and an alkyl methacrylate, a copolymer of acrylic acid and methacrylic acid or an alkyl acrylate or alkyl methacrylate, a polyvinyl acetal, a polyvinyl butyral, an alkyl-substituted poly-N-vinylpyrrolidone, and an alkyl ester of a copolymer of an olefin and maleic anhydride, with at least one substance which has antimycotic activity selected from the group consisting of tioconazole, econazole, oxiconazole, miconazole, tolnaftate and naftifine hydrochloride, as well as, where appropriate, with other components customary for the preparation of nail lacquer.

12. A process which comprises using one or more substance having antimycotic activity selected from the group consisting of tioconazole, econazole, oxiconazole, miconazole, tolnaftate and naftifine hydrochloride as an additive in a nail lacquer containing at least one film-former which is insoluble in water.

* * * * *